(12) United States Patent
Rooks et al.

(10) Patent No.: US 8,906,018 B2
(45) Date of Patent: Dec. 9, 2014

(54) SURGICAL FORCEPS

(75) Inventors: Kathy E. Rooks, Aurora, CO (US); Glenn A. Horner, Boulder, CO (US); Duane E. Kerr, Loveland, CO (US); Jeffrey R. Townsend, Loveland, CO (US); William H. Nau, Jr., Longmont, CO (US); David M. Garrison, Longmont, CO (US); Edward M. Chojin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1088 days.

(21) Appl. No.: 12/906,672

(22) Filed: Oct. 18, 2010

(65) Prior Publication Data

US 2012/0095460 A1    Apr. 19, 2012

(51) Int. Cl.
| | |
|---|---|
| A61B 18/18 | (2006.01) |
| A61B 17/295 | (2006.01) |
| A61B 18/14 | (2006.01) |
| A61B 17/28 | (2006.01) |
| A61B 18/00 | (2006.01) |
| A61B 17/29 | (2006.01) |
| A61B 17/32 | (2006.01) |

(52) U.S. Cl.
CPC ........... *A61B 18/1445* (2013.01); *A61B 17/295* (2013.01); *A61B 2018/0063* (2013.01); *A61B 17/28* (2013.01); *A61B 2017/2926* (2013.01); *A61B 2018/00601* (2013.01); *A61B 18/1442* (2013.01); *A61B 17/320092* (2013.01); *A61B 17/320068* (2013.01); *A61B 2018/1455* (2013.01)
USPC ............................... 606/52; 606/51; 606/207

(58) Field of Classification Search
USPC ....................... 606/37, 51, 52, 207
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

PCT International Search Report, for PCT Application No. PCT/US2012/052738, dated Dec. 26, 2012.

(Continued)

*Primary Examiner* — Linda Dvorak
*Assistant Examiner* — Jocelyn D Ram

(57) ABSTRACT

A forceps includes an end effector assembly having first and second jaw members moveable with respect to one another between an open position and a closed position. A knife channel having a body and a base is defined within each jaw member. A knife assembly includes a knife having a bifurcated distal end. The bifurcated end includes first and second cutting members each defining an opposed cutting surface and having a tab at a free end thereof for translation through the base of a knife channel. The knife is translatable into the channels when the jaw members are in the closed position such that the cutting members are approximated when translated through the channels. The knife is also translatable into the channels when the jaw members are in the open position such that the cutting members are flexed apart when translated through the jaw members.

6 Claims, 6 Drawing Sheets

(56) References Cited

U.S. PATENT DOCUMENTS

| | | | |
|---|---|---|---|
| D295,894 S | 5/1988 | Sharkany et al. | |
| D298,353 S | 11/1988 | Manno | |
| D299,413 S | 1/1989 | DeCarolis | |
| 5,171,250 A | 12/1992 | Yoon | |
| 5,219,354 A | 6/1993 | Choudhury et al. | |
| D343,453 S | 1/1994 | Noda | |
| D348,930 S | 7/1994 | Olson | |
| D349,341 S | 8/1994 | Lichtman et al. | |
| 5,352,222 A | 10/1994 | Rydell | |
| D354,564 S | 1/1995 | Medema | |
| D358,887 S | 5/1995 | Feinberg | |
| 5,554,164 A | 9/1996 | Wilson et al. | |
| 5,562,699 A | 10/1996 | Heimberger et al. | |
| 5,599,350 A * | 2/1997 | Schulze et al. | 606/51 |
| D384,413 S | 9/1997 | Zlock et al. | |
| 5,766,166 A | 6/1998 | Hooven | |
| 5,797,941 A * | 8/1998 | Schulze et al. | 606/171 |
| D402,028 S | 12/1998 | Grimm et al. | |
| D416,089 S | 11/1999 | Barton et al. | |
| 5,984,938 A * | 11/1999 | Yoon | 606/170 |
| D424,694 S | 5/2000 | Tetzlaff et al. | |
| D425,201 S | 5/2000 | Tetzlaff et al. | |
| 6,174,309 B1 | 1/2001 | Wrublewski et al. | |
| 6,221,039 B1 | 4/2001 | Durgin et al. | |
| D449,886 S | 10/2001 | Tetzlaff et al. | |
| D454,951 S | 3/2002 | Bon | |
| D457,958 S | 5/2002 | Dycus et al. | |
| D457,959 S | 5/2002 | Tetzlaff et al. | |
| 6,398,741 B2 | 6/2002 | Niizeki et al. | |
| D465,281 S | 11/2002 | Lang | |
| D466,209 S | 11/2002 | Bon | |
| 6,676,660 B2 | 1/2004 | Wampler et al. | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 7,011,657 B2 | 3/2006 | Truckai et al. | |
| D525,361 S | 7/2006 | Hushka | |
| 7,101,371 B2 | 9/2006 | Dycus et al. | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| 7,156,846 B2 | 1/2007 | Dycus et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 2004/0087943 A1 | 5/2004 | Dycus et al. | |
| 2007/0260242 A1 | 11/2007 | Dycus et al. | |
| 2008/0004616 A1 | 1/2008 | Patrick | |
| 2008/0015567 A1 | 1/2008 | Kimura | |
| 2008/0045947 A1 | 2/2008 | Johnson et al. | |
| 2010/0179539 A1 | 7/2010 | Nau, Jr. | |
| 2010/0274244 A1 * | 10/2010 | Heard | 606/45 |
| 2011/0054468 A1 * | 3/2011 | Dycus | 606/45 |
| 2011/0238065 A1 * | 9/2011 | Hunt et al. | 606/45 |
| 2013/0150842 A1 * | 6/2013 | Nau et al. | 606/13 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 19738457 | 1/2009 |
| DE | 10 2008 018406 | 7/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 6-285078 | 10/1994 |
| JP | 6-511401 | 12/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2001-190564 | 7/2001 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, Thomas P. Ryan.
U.S. Appl. No. 12/336,970, filed Dec. 17, 2008, Paul R. Sremcich.
U.S. Appl. No. 12/576,380, filed Oct. 9, 2009, Wayne Siebrecht.
U.S. Appl. No. 12/607,191, William H. Nau Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Horner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.

(56) References Cited

OTHER PUBLICATIONS

U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/004,984, filed Jan. 12, 2011, David M. Garrison.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/048,679, filed Mar. 15, 2011, Paul Guerra.
U.S. Appl. No. 13/075,847, filed Mar. 30, 2011, Gary M. Couture.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report Ep 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report Ep 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181969.6 dated Feb. 4, 2011.
Int'l Search Report EP 10 191320.0 dated Feb. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.

(56) References Cited

OTHER PUBLICATIONS

Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

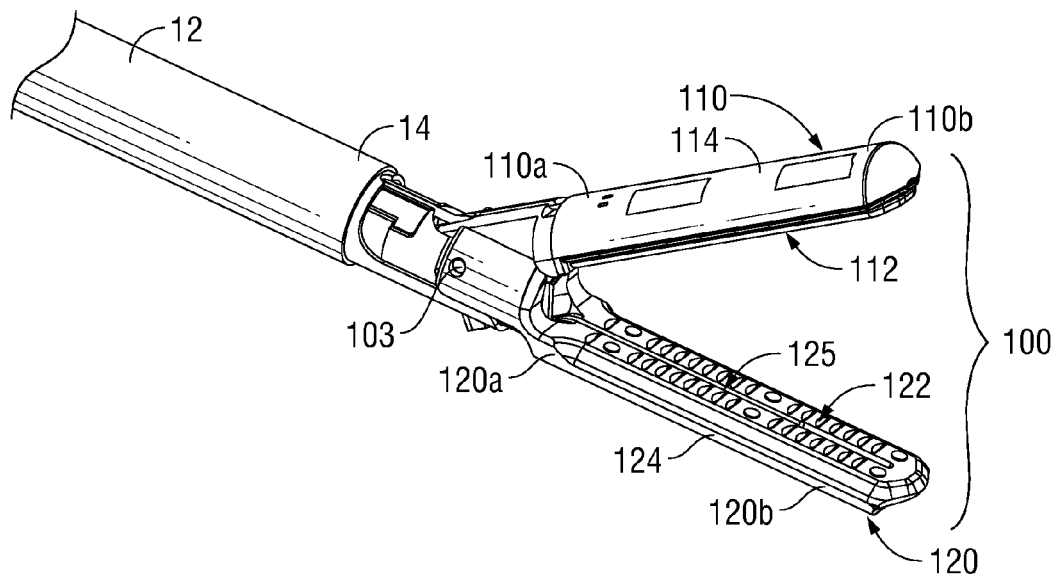
FIG. 2
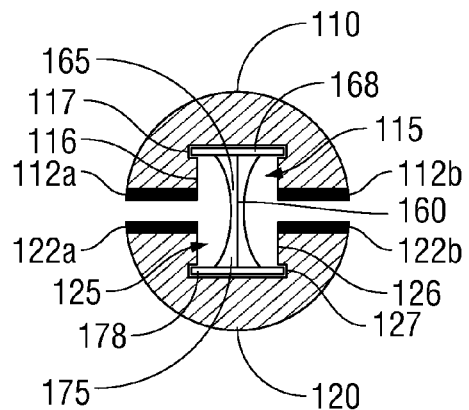
FIG. 3
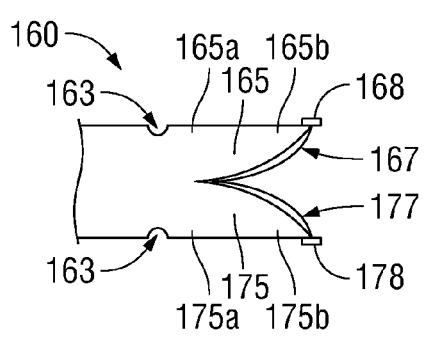 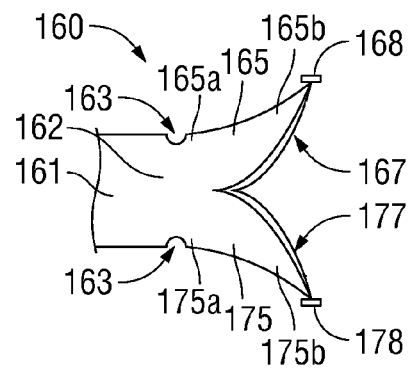
FIG. 4A  FIG. 4B

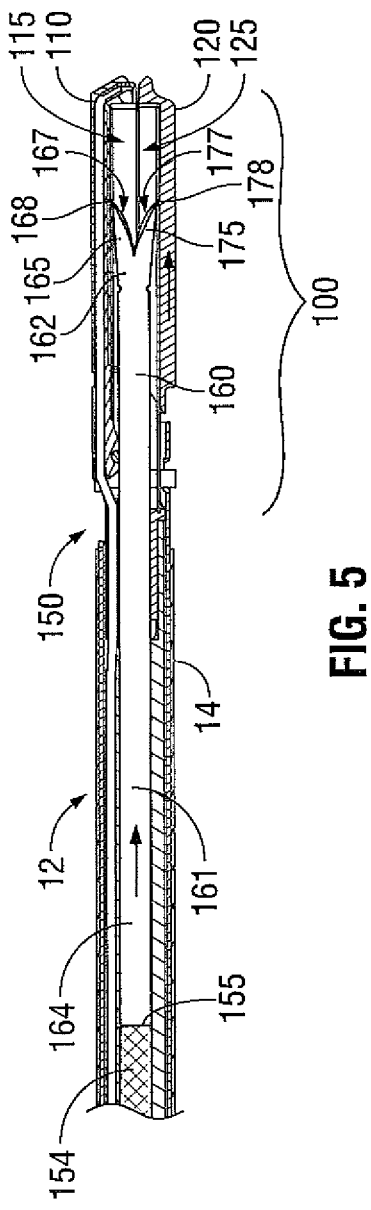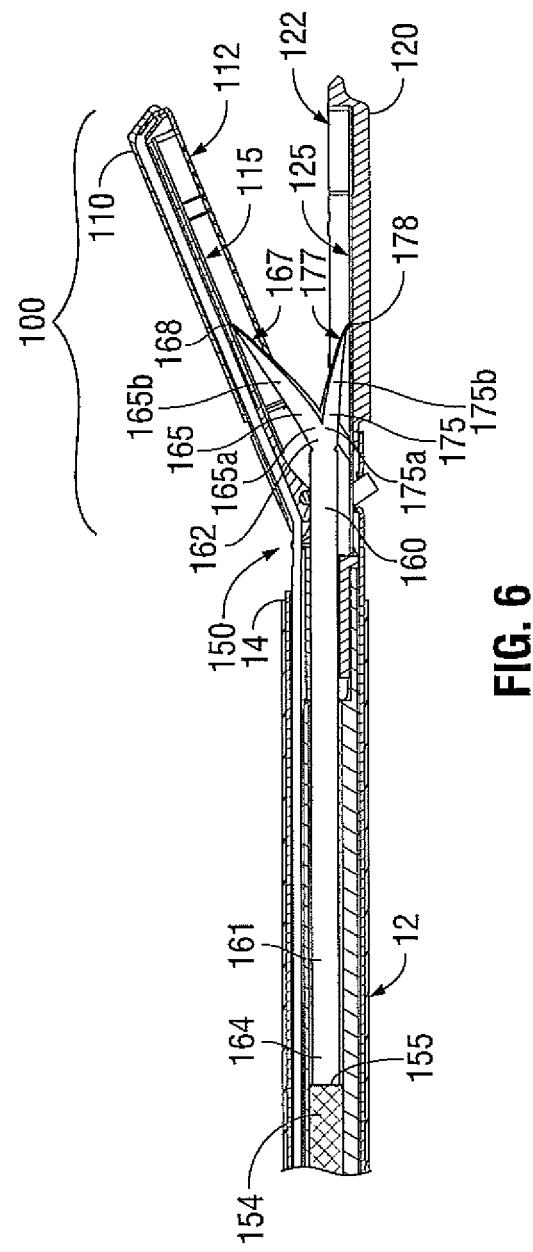

SURGICAL FORCEPS

BACKGROUND

The present disclosure relates to surgical instruments. More particularly, the present disclosure relates to surgical forceps for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a forceps including an end effector assembly. The end effector assembly includes first and second jaw members disposed in opposed relation relative to one another. One or both of the jaw members is moveable with respect to the other between an open position and a closed position for grasping tissue therebetween. A knife channel is defined within each of the jaw members and extends longitudinally therealong. Each knife channel includes a body portion and a base portion. A knife assembly is also provided. The knife assembly includes a knife having a bifurcated distal end. The knife is configured for translation through the body portions of the knife channels. The bifurcated distal end of the knife includes first and second cutting members. Each cutting member defines an opposed cutting surface and has a tab disposed at a free end thereof opposite the opposed cutting surface. Each tab is configured for translation through the base portion of one of the knife channels. The knife is translatable into the knife channels of the jaw members when the jaw members are in the open or the closed position. The first and second cutting members of the knife are in an approximated position with respect to one another when translated through the knife channels of the jaw members when the jaw members are in the closed position. The cutting members are flexed apart from one another in a spaced relation when translated through the knife channels of the jaw members when the jaw members are in the open position.

In one embodiment, the first and second cutting members are resiliently moveable between the spaced-apart and approximated positions. The first and second cutting members may also be biased toward the approximated position.

In another embodiment, when the first and second cutting members are disposed at a distal end of the knife channels, the jaw members may be moved between the open and closed positions to produce a scissor-cutting effect on tissue disposed between the jaw members.

In yet another embodiment, when the first and second cutting members are translated through the knife channels with the jaw members in the closed position, the cutting members produce a dissection-cutting effect on tissue disposed between the jaw members.

In still another embodiment, one or both of the jaw members includes an electrically conductive tissue sealing surface disposed on an opposed surface thereof. The sealing surface(s) is adapted to connect to a source of electrosurgical energy for sealing tissue disposed between the jaw members.

In accordance with another embodiment of the present disclosure, an end effector assembly for use with a forceps is provided. The end effector assembly includes first and second jaw members disposed in opposed relation relative to one another. One or both jaw members is moveable with respect to the other between a spaced-apart position and an approximated position for grasping tissue therebetween. A cutting member is disposed within one of the jaw members. The cutting member is selectively deployable from a retracted position to an extended position. In the retracted position, the cutting member is nested within a recessed portion defined within the jaw member. In the extended position, the cutting member is deployed between the jaw members to cut tissue grasped therebetween.

In still yet another embodiment, the cutting member is coupled to the jaw members by an actuation mechanism. The actuation mechanism may include a spring coupled to an actuator.

In another embodiment, the cutting member is biased toward the retracted position. Further, the cutting member may be configured to return to the retracted position upon movement of the jaw members from the approximated position to the spaced-apart position.

In yet another embodiment, one or both of the jaw members includes an electrically conductive tissue sealing surface disposed on an opposed surface thereof. The sealing surface(s) is adapted to connect to a source of electrosurgical energy for sealing tissue disposed between the jaw members.

In accordance with yet another embodiment of the present disclosure, an end effector assembly for use with a forceps is provided. The end effector assembly includes first and second jaw members disposed in opposed relation relative to one another. One or both of the jaw members is moveable with respect to the other between a spaced-apart position and an approximated position for grasping tissue therebetween. A transducer is disposed within one of the jaw members and includes a cutting member coupled thereto. The cutting member is configured to extend between the jaw members when the jaw members are moved to the approximated position.

Upon activation of the transducer, the transducer is configured to vibrate the cutting member with respect to the jaw members to cut tissue grasped between the jaw members.

The transducer may be a piezoelectric transducer or a high frequency transducer.

In yet another embodiment, the transducer is configured to vibrate the cutting member in at least one of a vertical and a horizontal direction.

In accordance with still yet another embodiment of the present disclosure, a forceps is provided. The forceps includes a housing having a shaft attached thereto and an end effector assembly disposed at a distal end of the shaft. The end effector assembly includes first and second jaw members disposed in opposed relation relative to one another. One or both of the jaw members is moveable with respect to the other between a spaced-apart position and an approximated position for grasping tissue therebetween. A tubular member is disposed within the shaft. The tubular member includes a cutting edge formed at a distal end thereof. The tubular member defined a lumen therethrough and is configured for passage of a fluid therein. The tubular member is translatable from a retracted position to an extended position. In the retracted position, the tubular member is disposed within the shaft. In the extended position the tubular member is translated distally between the jaw members such that a portion of the tubular member extends distally from a distal end of the jaw members.

In one embodiment, the tubular member is a hypotube.

In still another embodiment, a channel is defined within one or both of the jaw members. The channel(s) is configured for translation of the tubular member therethrough.

In yet another embodiment, one or both of the jaw members includes an electrically conductive tissue sealing surface disposed on an opposed surface thereof. The sealing surface(s) is adapted to connect to a source of electrosurgical energy for sealing tissue disposed between the jaw members.

BRIEF DESCRIPTION OF THE DRAWINGS

Various embodiments of the presently disclosed forceps are described herein with reference to the drawings, wherein:

FIG. 2 is an enlarged, perspective view of the end effector assembly of the forceps of FIG. 1;

FIG. 3 is a front, cross-sectional view of the end effector assembly of FIG. 2;

FIG. 4A is a side view of a knife shown in an approximated position and configured for use with the end effector assembly of FIG. 2;

FIG. 4B is a side view of the knife of FIG. 4A shown in a spaced-apart position;

FIG. 5 is a side, cross-sectional view of the end effector assembly of FIG. 2 in a closed position showing the knife of FIG. 4A translating therethrough in an approximated position;

FIG. 6 is a side, cross-sectional view of the end effector assembly of FIG. 2 in an open position showing the knife of FIG. 4A translating therethrough in a spaced-apart position;

DETAILED DESCRIPTION

Figure 1:
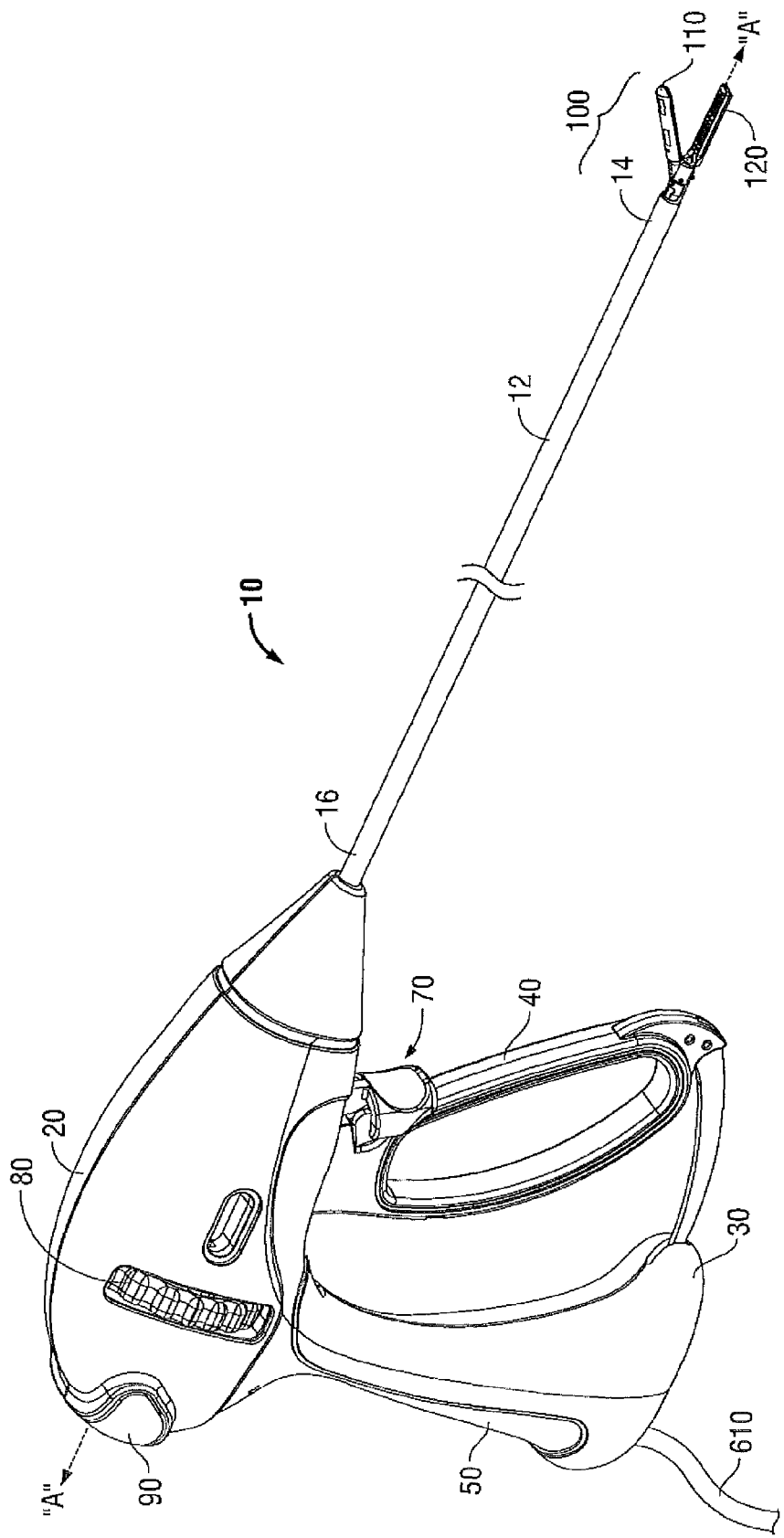
FIG. 1 is a perspective view of a forceps including an end effector assembly in accordance with the present disclosure.

Embodiments of the presently disclosed surgical instrument are described in detail with reference to the drawing figures wherein like reference numerals identify similar or identical elements. As used herein, the term "distal" refers to the portion that is being described that is further from a user, while the term "proximal" refers to the portion that is being described that is closer to a user.

Turning now to FIG. 1, a forceps 10 is provided including a housing 20, a handle assembly 30, a rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. Housing 20 includes two halves that house the internal working components of forceps 10. Although shown as an endoscopic surgical instrument, forceps 10 may also be configured as an open, hemostat-style surgical instrument.

End effector assembly 100 includes a pair of opposed jaw members 110 and 120. End effector assembly 100 is designed as a unilateral assembly, i.e., jaw member 120 is fixed relative to shaft 12 and jaw member 110 is moveable about a pivot 103 (FIG. 2) relative to jaw member 120. However, either, or both jaw members 110, 120 may be moveable with respect to the other.

Forceps 10 also includes an electrosurgical cable 610 that connects forceps 10 to a generator (not shown). Cable 610 has sufficient length to extend through shaft 12 in order to provide electrical energy to at least one of jaw members 110 and 120 of end effector assembly 100. Alternatively, forceps 10 may be configured as a battery powered instrument.

With continued reference to FIG. 1, handle assembly 30 includes a fixed handle 50 and a moveable handle 40. Fixed handle 50 is integrally associated with housing 20 and moveable handle 40 is moveable relative to fixed handle 50. Moveable handle 40 of handle assembly 30 is ultimately connected to a drive assembly (not shown) that, together, mechanically cooperate to impart movement of jaw members 110 and 120 between an open, or spaced-apart position and a closed, or approximated position.

Rotating assembly 80 is integrally associated with housing 20 and is rotatable in either direction about a longitudinal axis "A-A" to rotate end effector assembly 100 and, thus, jaw members 110, 120, with respect to housing 20 about longitudinal axis "A-A."

Referring now to FIG. 2, one embodiment of an end effector assembly for use with forceps 10 (FIG. 1) is shown generally identified by reference numeral 100. As mentioned above, end effector assembly 100 is disposed at distal end 14 of shaft 12 and includes first and second jaw members 110, 120, respectively, disposed in opposing relation relative to one another. Each jaw member 110, 120 includes a respective electrically conductive tissue sealing surface 112, 122 disposed on an opposed surface thereof and an outer jaw housing 114, 124, respectively.

As best shown in FIG. 3, each jaw member 110, 120 includes a knife channel 115, 125, respectively, defined therein and extending therealong. Knife channels 115, 125 of jaw members 110, 120, respectively, bisect sealing surfaces 112, 122 of jaw members 110, 120, respectively, into longitudinal sealing surface sections 112a, 112b and 122a, 122b, respectively, that are disposed on either side of respective knife channels 115, 125. Further, knife channel 115 includes a body portion 116 and a base portion 117 configured such that knife channel 115 defines a "T"-shaped configuration. Similarly, knife channel 125 includes a body portion 126 and a base portion 127 and defines a "T"-shaped configuration. Upon movement of jaw members 110, 120 to the approximated position, the opposed "T"-shaped knife channels 115, 125 of jaw members 110, 120, respectively, cooperate to form an "I"-shaped channel extending longitudinally through jaw members 110, 120.

FIGS. 4A-4B show a knife 160 of knife assembly 150 (FIGS. 5-6) that is configured for translation from an initial position within shaft 12 (FIG. 2) through knife channels 115, 125 of jaw members 110, 120, respectively, to cut tissue disposed therebetween. Knife 160 includes an elongated body 161 and a bifurcated distal end 162. Bifurcated distal end 162 of knife 160 includes first and second cutting members 165, 175, respectively, extending distally from elongated body 161 of knife 160. More specifically, each cutting member 165, 175 includes a respective fixed end 165a, 175a and a respective free end 165b, 175b. Each cutting member 165, 175 also includes an opposed cutting surface, or edge 167, 177, respectively. A tab 168, 178 is disposed opposite cutting edges 167, 177 on each of cutting members 165, 175, respectively, at respective free ends 165b, 175b thereof.

As shown in FIGS. 5 and 6, proximal end 164 of knife 160 is fixedly-engaged to a distal end 155 of a drive bar 154 that extends through shaft 12, ultimately coupling to trigger 70 (FIG. 1) for selectively translating knife 160 between a retracted position, wherein knife 160 is disposed within shaft 12 (FIG. 2), and an extended position, wherein knife 160 is advanced distally through channels 115, 125 of jaw members 110, 120, respectively (FIGS. 5 and 6).

As mentioned above, knife 160 is configured for translation through knife channels 115, 125 of jaw members 110, 120, respectively. Specifically, tabs 168, 178 are configured for translation through respective base portions 117, 127 of channels 115, 125, while cutting members 165, 175 are configured for translation through body portions 116, 126 of channels 115, 125 of jaw members 110, 120, respectively. Accordingly, tabs 168, 178 and base portions 117, 127 may be complementarily-dimensioned such that tabs 168, 178 of respective cutting members 165, 175 of knife 160 are retained within respective base portions 117, 127 of channels 115, 125 during translation therethrough. Retaining tabs 168, 178 within base portions 117, 127 of channels 115, 125, respectively, helps ensure that knife 160 is consistently translated through channels 115, 125 of jaw members 110, 120, respectively, to cut tissue disposed therebetween. In other words, base portions 117, 127 of channels 115, 125, respectively, serve as tracks for guiding the translation of tabs 168, 178 of cutting members 165, 175, respectively, of knife 160 through channels 115, 125 of respective jaw members 110, 120.

With reference again to FIGS. 4A and 4B, cutting members 165, 175 of knife 160 are moveable with respect to one another between an approximated position (FIG. 4A) and a spaced-apart position (FIG. 4B). In the approximated position, as shown in FIG. 4A, cutting members 165, 175 define a relatively small gap between opposed cutting edges 167, 177. In the spaced-apart position, on the other hand, as shown in FIG. 4B, cutting members 165, 175 are flexed apart from one another to define a relatively large gap between opposed cutting edges 167, 177. Cutting members 165, 175 may be formed from a resilient, spring-like material to facilitate movement of cutting members 165, 175 between the approximated position (FIG. 4A) and the spaced-apart position (FIG. 4B). Further, detents 163 may be defined within elongated body 161 of knife 160 toward distal end 162 thereof to facilitate movement of cutting members 165, 175 between the approximated position (FIG. 4A) and the spaced-apart position (FIG. 4B). Alternatively, cutting members 165, 175 may be pivotably engaged at fixed ends 165a, 175a, respectively, thereof or may be engaged in any other suitable fashion such that cutting members 165, 175 are moveable with respect to one another between an approximated position (FIG. 4A) and a spaced-apart position (FIG. 4B). Additionally, cutting members 165, 175 may be biased toward the approximated position or, alternatively, may be biased toward the spaced-apart position.

Referring now to FIGS. 5 and 6 in conjunctions with FIGS. 4A and 4B, knife 160 may be translated through knife channels 115, 125 of respective jaw members 110, 120 when jaw members 110, 120 are disposed in either of the closed position (FIG. 5) or the open (FIG. 6) position. When jaw members 110, 120 are in the closed position, as shown in FIG. 5, channels 115, 125 are substantially parallel with one another and are approximated with respect to one another. Accordingly, when knife 160 is translated through channels 115, 125 when jaw members 110, 120 are in the closed position, the retention of tabs 168, 178 within respective base portion 117, 127 of channels 115, 125 maintains cutting members 165, 175 in the approximated position (FIG. 4A), substantially parallel to one another. On the other hand, when jaw members 110, 120 are moved to the open position, as shown in FIG. 6, channels 115, 125 are no longer parallel but, rather, are increasingly spaced-apart from one another from proximal ends 110a, 120a (FIG. 2) to distal ends 110b, 120b (FIG. 2) of jaw members 110, 120, respectively. Thus, due to the retention of tabs 168, 178 of cutting members 165, 175 within base portions 117, 127 of respective channels 115, 125, cutting members 165, 175 are increasingly flexed apart from one another from the approximated position (FIG. 4A) to the spaced-apart position (FIG. 4B) as knife 160 is translated distally through knife channels 115, 125 when jaw members 110, 120 are in the open position.

The use and operation of end effector assembly 100 will be described with reference to FIGS. 2-6. In use, end effector assembly 100 is adapted to operate in at least three different modes: a "sealing" mode, a "dissecting" mode, and a "scissor-cutting," or "shearing" mode. Any of these modes may be performed independently or in conjunction with any other modes of end effector assembly 100.

Regarding the "sealing" mode, end effector assembly 100 may be used to seal tissue. Initially, with jaw members 110, 120 in the open position, end effector assembly 100 is positioned such that tissue to be sealed is disposed between jaw members 110, 120. Jaw members 110, 120 may then be moved to the closed position, e.g., by squeezing moveable handle 40 (FIG. 1) with respect to fixed handle 50 (FIG. 1), to grasp tissue between sealing surfaces 112, 122 of jaw members 110, 120, respectively. Next, electrosurgical energy is supplied to sealing surfaces 112 and/or 122 and is conducted through tissue disposed therebetween for sealing tissue grasped between sealing surfaces 112, 122. Accordingly, a tissue seal may be effected substantially along a width of sealing surfaces 112, 122 of jaw members 110, 120, respectively.

Referring now to FIG. 5, the "dissecting" mode of end effector assembly 100 may be used to dissect, or divide tissue along the previously formed tissue seal (or may otherwise be used to dissect tissue grasped between jaw members 110, 120). With jaw members 110, 120 in the closed position grasping tissue between sealing surfaces 112, 122, respectively, knife 160 of knife assembly 150 may be advanced distally from shaft 12 and through knife channels 115, 125 of jaw members 110, 120, respectively, to divide tissue disposed between sealing surfaces 112, 122. More particularly, upon actuation, e.g., upon depression of trigger 70 (FIG. 1), drive bar 154 is urged distally, thereby translating knife 160 distally through end effector assembly 100.

As knife 160 is translated distally from shaft 12 into end effector assembly 100, tabs 168, 178 of cutting members 165, 175 of bifurcated distal end 162 of knife 160 are retained within and translated through respective base portions 117, 127 of channels 115, 125, as best shown in FIG. 3. At the same time, cutting members 165, 175 are translated through respective body portions 116, 126 of channels 115, 125. With jaw members 110, 120 in the closed position, channels 115, 125 cooperate to define the "I"-shaped channel discussed above. Accordingly, base portions 117, 127 of channels 115, 125 are substantially parallel and approximated with respect to one another when jaw members 110, 120 are in the closed position. Thus, as mentioned above, when knife 160 is advanced distally through the closed jaw members 110, 120, the retention of tabs 168, 178 of cutting members 165, 175 within base portions 117, 127 of respective channels 115, 125, maintains cutting members 165, 175 in the approximated position (see FIG. 4A).

As knife 160 is translated further distally through end effector assembly 100, opposed cutting edges 167, 177 of cutting members 165, 175 are advanced through tissue grasped between sealing surfaces 112, 122 of jaw members 110, 120, respectively, to divide tissue disposed therebetween. The bifurcated configuration of cutting members 165, 175 of knife 160 facilitates dissection of tissue by providing two opposed cutting edges 167, 177, creating a larger cutting area, and also facilitating dissection of tissue by funneling tissue into the gap defined between cutting members 165, 175, e.g., between cutting edges 167, 177, allowing for dissection of tissue substantially along the entire length of cutting edges 167, 177.

Referring now to FIG. 6, the "scissor-cutting" or "shearing" mode of end effector assembly 100 is described. Initially, jaw members 110, 120 are moved to the open position and are positioned such that tissue to be cut is disposed therebetween. In this open position, as mentioned above, channels 115, 125 are increasingly flexed, or spaced-apart from one another from proximal ends 110a, 120a to distal ends 110b, 120b of jaw members 110, 120, respectively. With jaw members 110, 120 in this open position, trigger 70 (FIG. 1) is actuated to advance drive bar 154 distally, thereby translating knife 160 distally through channels 115, 125 of jaw members 110, 120, respectively. More specifically, knife 160 is translated distally into end effector assembly 100 such that tabs 168, 178 of respective cutting members 165, 175 are translated through base portions 117, 127 of channels 115, 125 of jaw members 110, 120, respectively. The retention of tabs 168, 178 within base portions 117, 127 of respective channels 115, 125 cause cutting members 165, 175 to increasingly flex apart from one another to the spaced-apart position (FIG. 4B) as knife 160 is translated from proximal ends 110a, 120a to distal end 110b, 120b of jaw members 110, 120, respectively.

As shown in FIG. 6, when knife 160 is translated through end effector assembly 100 with jaw members 110, 120 in the open position, end effector assembly 100 defines an "open-scissor" configuration. More particularly, opposed cutting edges 167, 177 of respective cutting members 165, 175 extend inwardly toward one another from channels 115, 125, respectively, to define the scissor-cutting edges 167, 177 of the scissor blades (jaw members 110, 120). End effector assembly 100 may include a locking mechanism (not shown) for fixing cutting members 165, 175 in this extended position wherein cutting edges 167, 177 act as the scissor-cutting edges 167, 177 of jaw members 110, 120, respectively.

From the position shown in FIG. 6, end effector assembly 100 may be advanced distally with respect to tissue to dissect through tissue, or, alternatively, jaw members 110, 120 may be moved between the open and closed positions for scissor-cutting tissue disposed between jaw members 110, 120. More particularly, during scissor-cutting, cutting members 165, 175 are moved between the spaced-apart position and the approximated position as jaw members 110, 120 are moved between the open and closed positions. As a result, opposed cutting edges 167, 177 are moved between the spaced-apart position and the approximated position, cutting tissue disposed therebetween in a scissor-like fashion.

Another embodiment of an end effector assembly, end effector assembly 200, configured for use with forceps 10 (FIG. 1) is shown in FIGS. 7A-7D. As in the previous embodiment, end effector assembly 200 includes first and second jaw members 210, 220, respectively, disposed in opposed relation relative to one another. One (or both) of jaw members 210, 220 is moveable with respect to the other about a pivot 203 between an open, or spaced-apart position and a closed, or approximated position for grasping tissue therebetween. Each jaw member 210, 220 also includes an electrically conductive tissue sealing surface 212, 222, respectively, disposed on an opposed surface thereof and a respective outer jaw housing 214, 224.

One (or both) of the jaw members, e.g., jaw member 210, includes a cutting assembly 250 disposed within a cavity 216 defined therein. Cutting assembly 250 includes a cutting member 260, an actuation mechanism, e.g., a spring 272 (or a wire or link (not shown)) and a cable 274 (or shaft (not shown)) coupled to cutting assembly 250, extending through shaft 12 (FIG. 1) and ultimately coupling to trigger 70 (FIG. 1) for selectively deploying cutting member 260 from a retracted position (FIG. 7A) to an extended position (FIG. 7C) for cutting tissue disposed between jaw members 210, 220. Jaw member 220 may also include a cavity, or channel 226 defined therein to permit full extension of cutting member 260 through the gap "G" defined between jaw members 210, 220 to cut tissue disposed therebetween.

In the illustrated embodiment, cutting member 260 defines a triangular cross-sectional profile and includes a serrated bottom cutting edge 262, although other cross-sectional and/or cutting edge configurations may be provided. Cutting member 260 is coupled at a proximal end thereof to the actuation mechanism, e.g., spring 272. The actuation mechanism may include hydraulics, cables, linkages, or any other spring-like mechanism capable of deploying cutting member 260 from the retracted position to the extended position. Alternatively, the actuation mechanism may include a shape memory element that is elongated upon heating to deploy cutting member 260 from the retracted position to the extended position. Cable 274 is coupled to spring 272 and extends proximally from jaw member 210, through shaft 12 (FIG. 1), ultimately coupling to trigger 70 (FIG. 1) for user-controlled activation of cutting assembly 250. Upon activation, e.g., upon depression of trigger 70 (FIG. 1) cable 274 mechanically, electrically, or electro-mechanically actuates the actuation mechanism, e.g., spring 272, to deploy cutting member 260 from the retracted position (FIG. 7A) to the extended position (FIG. 7C).

Figure 7A:
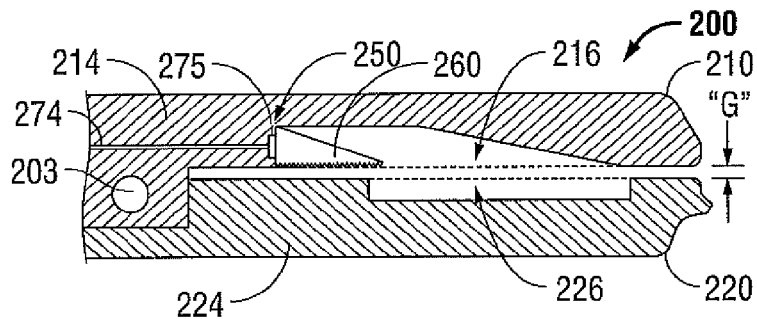
FIG. 7A is a side, cross-sectional view of an end effector assembly configured for use with the forceps of FIG. 1 according to another embodiment of the present disclosure showing a cutting member in a retracted position.

As shown in FIG. 7A, jaw members 210, 220 are disposed in the approximated position and cutting member 260 is disposed in the retracted position. More particularly, in the retracted position, cutting member 260 is nested within cavity 216 defined within jaw member 210. Cavity 216 may define a triangular cross-sectional profile that is sloped complementarily to cutting member 260 such that, in the retracted position, a proximal side of cutting member substantially mates with a proximal surface of cavity 216 and such that an angled top side of cutting member 260 substantially mates with an angled top surface of cavity 216. Further, cavity 216 may be dimensioned such that, in the retracted position, cutting member 260 is nested completely therein. In other words, when cutting member 260 is in the retracted position, bottom cutting surface 262 is completely disposed within cavity 216 and, thus, does not extend, or protrude into the gap space "G" defined between jaw members 210, 220. As can be appreciated, such a configuration prevents cutting member 260 from interfering with jaw members 210, 220 during the grasping and/or sealing of tissue.

Spring 272 (or other actuation mechanism) may be biased toward the extended position, thus biasing cutting member 260 toward the extended position. Accordingly, with spring 272 biased toward the extended position, a releasable locking mechanism 275 may be provided for releasably locking cutting member 260 in the retracted position (FIG. 7A) against the bias of spring 272. Thus, when cutting member 260 is locked in the retracted position, as shown in FIG. 7A, spring 272 is "set" or "armed" for deployment. Accordingly, upon unlocking of locking mechanism 275, e.g., upon actuation of cutting assembly 250, spring 272 and, thus, cutting member 260, are deployed to the extended position. Further, the releasable locking mechanism 275 may include one or more safety features configured to prevent inadvertent deployment of cutting member 260 such as, for example, an automatic locking feature that prevents deployment of cutting member 260 when jaw members 210, 220 are in the spaced-apart position.

In operation, with reference now to FIGS. 7A-7D, jaw members 210, 220 of end effector assembly 200 are configured for movement between the spaced-apart position and the approximated position for grasping tissue therebetween. With tissue grasped between jaw member 210, 220, as in the previous embodiment, electrosurgical energy may be supplied to one (or both) of opposed tissue sealing surfaces 212, 222 of jaw members 210, 220, respectively, and conducted through tissue to effect a tissue seal.

Figure 7B:
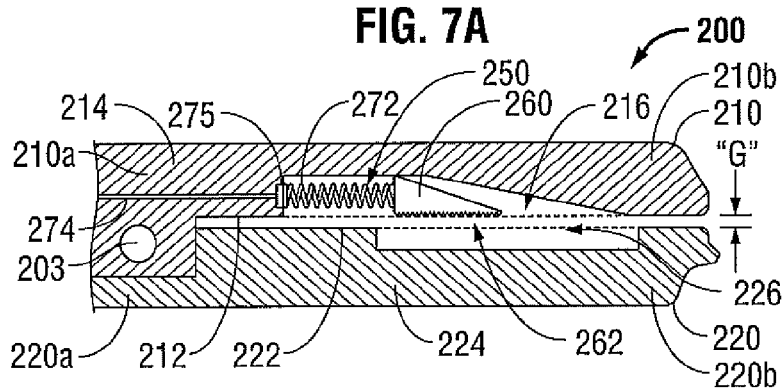
FIG. 7B is a side, cross-sectional view of the end effector assembly of FIG. 7A showing the cutting member being deployed from the retracted position.
Figure 7C:
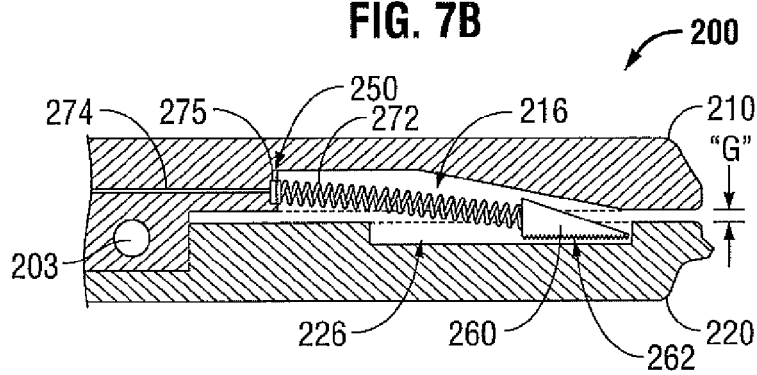
FIG. 7C is a side, cross-sectional view of the end effector assembly of FIG. 7A showing the cutting member in a deployed position.

Further, cutting assembly 250 is configured for cutting, or dividing tissue grasped between jaw members 210, 220. With tissue grasped between jaw members 210, 220, trigger 70 (FIG. 1) may be depressed to activate, or deploy spring 272 from the locked, retracted position. As best shown in FIG. 7B, upon release of locking mechanism 275, e.g., upon depression of trigger 70 (FIG. 1), the "armed" spring 272 is deployed, expanding back toward the biased, extended position from proximal ends 210a, 220a to distal ends 210b, 220b of jaw members 210, 220, respectively. With spring 272 disposed between the relatively fixed proximal surface of jaw member 210 that defines cavity 216 and the proximal side of the moveable cutting member 260, cutting member 260 is urged distally by the expansion of spring 272 back to the biased, or at-rest position. Additionally, due to the complementary triangular cross-sectional profile configurations of cavity 216 and cutting member 260, cutting member 260 is angled inwardly toward jaw member 220 upon distal translation of cutting member 260. In other words, as cutting member 260 is advanced distally, the angled top side of cutting member 260 is slid distally and inwardly, guided by and sliding along the angled top surface of cavity 216 such that cutting member 260 is extended into the gap space "G" defined between sealing surfaces 212, 222 of jaw members 210, 220, respectively.

With reference now to FIG. 7C, as cutting member 260 is slid further distally and inwardly, cutting member 260 eventually extends into the gap space "G" between jaw members 210, 220 and contacts tissue grasped between jaw members 210, 220. Serrated cutting edge 262 of cutting member 260 facilitates separation of tissue as cutting member 260 is advanced therethrough. More particularly, since cutting member 260 is translated inwardly toward jaw member 220 with respect to tissue in addition to being translated distally with respect to tissue, the serrations of cutting edge 262 "catch" and divide tissue in a single pass, functioning similarly to a single stroke of a serrated knife or a single stroke of a handsaw.

Spring 272 may be configured to exert a sufficient deployment force such that, upon actuation, e.g., upon depression of trigger 70 (FIG. 1), spring 272 urges cutting member 260 between jaw members 210, 220, completely through tissue disposed therebetween, and into channel 226 defined within jaw member 220. In other words, the stored energy in spring 272 (or other actuation mechanism), which is dependent upon the spring constant, must be great enough to urge cutting member 260 through tissue and into channel 226 of jaw member 220, overcoming the resistive forces of tissue as cutting member 260 is advanced therethrough. Accordingly, spring 272 (or other actuation mechanism) may be configured according to a particular size and/or composition of tissue or range of sizes and/or compositions of tissue to be sealed and cut.

Figure 7D:
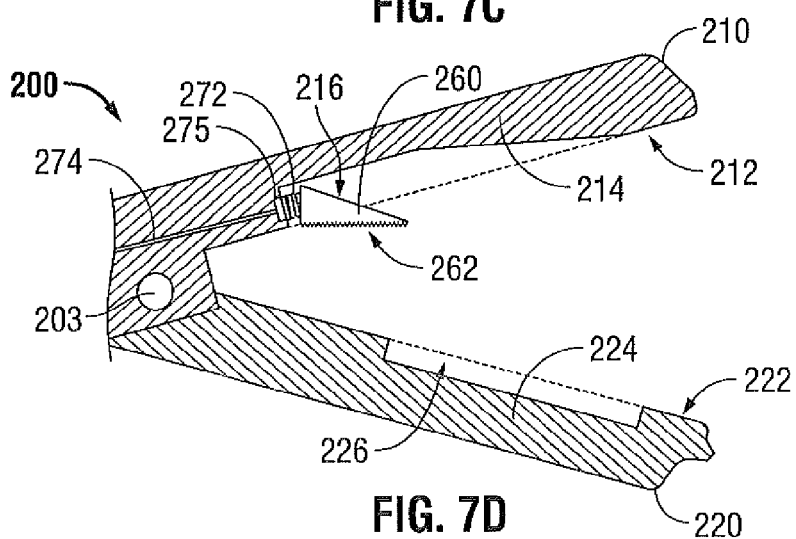
FIG. 7D is a side, cross-sectional view of the end effector assembly of FIG. 7A showing the cutting member returning to the retracted position.

With reference now to FIG. 7D, once tissue grasped between sealing surfaces 212, 222 of jaw members 210, 220, respectively, has been divided, e.g., once cutting member 260 has been deployed from cavity 216 of jaw member 210 (the retracted position), through tissue and into channel 226 of jaw member 220 (the extended position), jaw members 210, 220 may be moved from the approximated position to the spaced-apart position to release the sealed and divided tissue so that, ultimately, end effector assembly 200 may be removed from the surgical site.

Upon movement of jaw members 210, 220 to the spaced-apart position, cutting assembly 250 may be configured such that spring 272 and cutting member 260 are automatically returned to the retracted position. More particularly, upon return of moveable handle 40 (FIG. 1) with respect to fixed handle 50 (FIG. 1) to the initial position shown in FIG. 1, jaw members 210, 220 are moved to the spaced-apart position. As jaw members 210, 220 are increasingly spaced-apart from one another, locking mechanism 275 may be configured to reset, or "re-arm" spring 272, such that cutting member 260 is returned and fixed in the retracted position. Springs, hydraulics, or other mechanical, electro-mechanical, or electrical mechanisms may be included to facilitate the automatic return and rearming of spring 272 and cutting member 260 upon movement of jaw members 210, 220 to the spaced-apart position.

Alternatively, spring 272 may be returned to the retracted position by translating cable 274 distally to engage locking mechanism 275 with cutting member 260 and thereafter translating cable 274 proximally to retract cutting member 260. This may be accomplished by returning trigger 70 (FIG. 1) to its initial position. Further, cable 274 may be engaged to cutting member 260, in addition to, or in place of spring 272. In such an embodiment, cable 274 is translated between a proximal position and a distal position to move cutting member 260 between the retracted and extended positions, e.g., via selective actuation of trigger 70 (FIG. 1).

Figure 8:
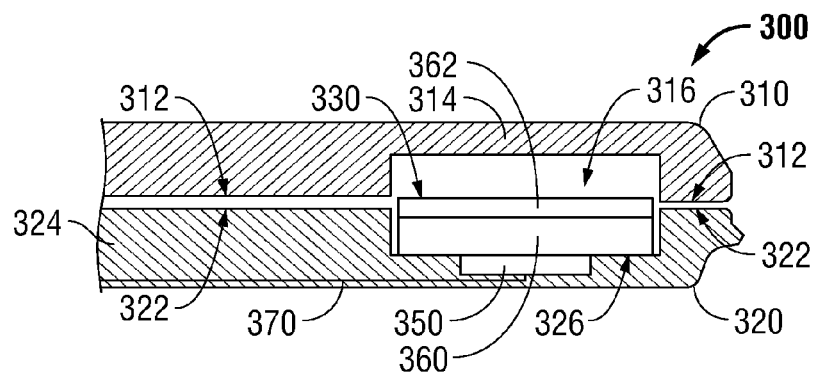
FIG. 8 is a side, cross-sectional view of an end effector assembly configured for use with the forceps of FIG. 1 according to yet another embodiment of the present disclosure showing a transducer disposed within a jaw member of the end effector assembly.

Referring now to the embodiment of FIG. 8, end effector assembly 300 is configured for use with forceps 10 (FIG. 1) and generally includes first and second jaw members 310, 320, respectively. Each jaw member 310, 320 includes an electrically conductive tissue sealing surface 312, 322, respectively, disposed on an opposed surface thereof and a respective outer jaw housing 314, 324. Jaw members 310, 320 are moveable between a spaced-apart position and an approximated position for grasping tissue therebetween.

One (or both) of the jaw members, e.g., jaw members 320, includes a cutting assembly 330 disposed within a cavity 326 defined therein. Cutting assembly 330 includes a transducer 350 positioned within cavity 326, a cutting member 360 disposed on and operably-coupled to transducer 350 and a control wire(s) 370 coupled to transducer 350. The cutting member 360 defines a cutting blade or edge 362 extending from cavity 326 between sealing surfaces 312, 322 of jaw members 310, 320, respectively. Control wire(s) 370 extends from jaw members 320 and through shaft 12 (FIG. 1) for electrically coupling transducer 350 to an energy source, e.g., electrosurgical cable 610 (FIG. 1), and to a switch 90 (FIG. 1) for selectively controlling transducer 350.

Jaw member 310 may include a cavity 316 defined therein and positioned opposite cutting assembly 330 to permit full approximation of jaw members 310, 320. In other words, upon movement of jaw members 310, 320 to the approximated position, cutting edge 362 of cutting member 360 of cutting assembly 330 may extend at least partially into cavity 316 such that cutting edge 362 does not contact sealing surface 312 of jaw member 310 when jaw members 310, 320 are in the approximated position. Further, cavity 316 of jaw member 310 may be configured to permit oscillation of cutting member 360 with respect to jaw members 310, 320 when jaw members 310, 320 are in the approximated position without cutting member 360 contacting jaw member 310.

Transducer 350 may be a piezoelectric transducer, a high-frequency transducer, or any other suitable transducer. Transducer 350 is configured to convert electrical energy supplied thereto, e.g., from control wire(s) 370 via a suitable energy source, into mechanical, or vibrational energy to oscillate, or vibrate cutting member 360 of cutting assembly 330. Transducer 350 may be configured to vibrate cutting member 360 in a vertical and/or a horizontal direction with respect to jaw members 310, 320. Transducer 350 may further be configured to operate in several modes, e.g., a high frequency mode and a lower frequency mode, and, accordingly, switch 90 (FIG. 1) may include an "off" setting, and one or more "on" settings corresponding to the different operational modes of transducer 350.

As in the previous embodiments, end effector assembly 300 may be used to seal tissue. In order to seal tissue, jaw members 310, 320 of end effector assembly 300 are moved from the spaced-apart position to the approximated position to grasp tissue therebetween. With tissue grasped between jaw members 310, 320, electrosurgical energy may be supplied to tissue sealing surfaces 312 and/or 322 of respective jaw members 310, 320 to seal tissue grasped therebetween. During tissue sealing, transducer 350 remains in "off" position. Thus, while tissue grasped between jaw members 310, 320 may contact cutting surface 362 of cutting member 360, tissue is substantially unaffected due to the stationary position of cutting surface 362 of cutting member 360 with respect to jaw members 310, 320.

Once tissue sealing is complete, and with tissue still grasped between sealing surfaces 312, 322 of jaw members 310, 320, respectively, switch 90 (FIG. 1) may be moved to the "on" position to activate transducer 350 for cutting tissue disposed between jaw members 310, 320. More specifically, as mentioned above, when transducer 350 is activated, electrical energy supplied thereto by wire(s) 370 is converted into mechanical energy for vibrating cutting member 360 and, thus, cutting edge 362 with respect to tissue grasped between jaw members 310, 320. Cutting edge 362 may include sharpened and/or textured features to facilitate cutting of tissue upon vibration of cutting member 360 with respect to tissue. Further, as vibrating cutting edge 362 contacts tissue and is vibrated with respect to the relatively fixed tissue, the friction created may thermally-enhance the cutting of tissue disposed between jaw members 310, 320.

As mentioned above, transducer 350 may be configured to operate in multiple modes corresponding to different frequencies and/or directions of motion. Accordingly, the operator may select the particular mode, e.g., high frequency, that is suitable for dividing a particular size and/or composition of tissue.

Figure 9A:
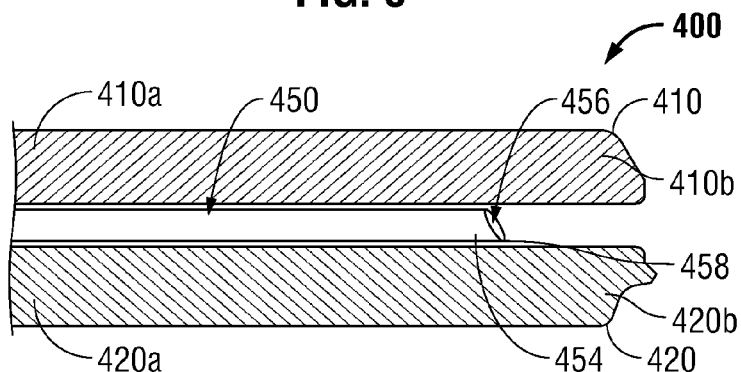
FIG. 9A is a side, cross-sectional view of an end effector assembly configured for use with the forceps of FIG. 1 according to still another embodiment of the present disclosure showing a tubular member advancing between jaw members of the end effector assembly.
Figure 9B:
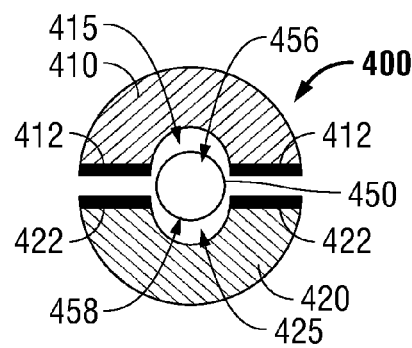
FIG. 9B is a front, cross-sectional view of the end effector assembly of FIG. 9A.
Figure 10:
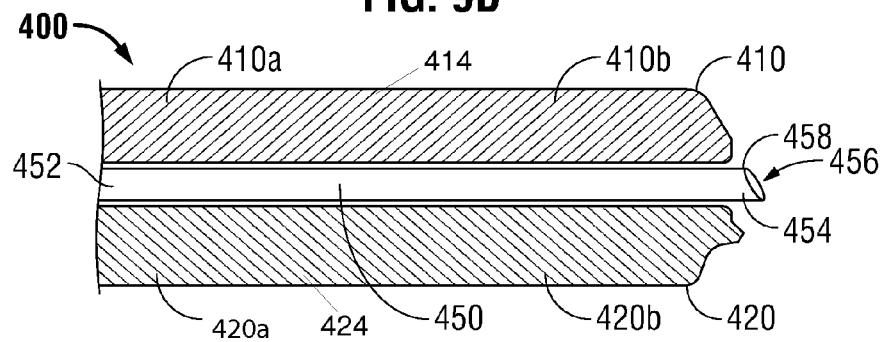
FIG. 10 is a side, cross-sectional view of the end effector assembly of FIG. 9A showing the tubular member extending beyond a distal end of the jaw members.

With reference now to FIGS. 9A-10, another end effector assembly configured for use with forceps 10 (FIG. 1) is generally identified by reference numeral 400. End effector assembly 400 includes first and second jaw members 410, 420, respectively, disposed in opposed relation relative to one another. Each jaw member 410, 420, includes a respective electrically conductive tissue sealing surface 412, 422 disposed on an opposed surface thereof and an outer jaw housing 414, 424, respectively. Jaw members 410 and/or 420 are moveable with respect to one another between a spaced-apart position and an approximated position for grasping tissue therebetween.

As shown in FIG. 9B, each jaw member 410, 420 also includes a complementary longitudinal channel 415, 425, respectively, defined therein that cooperate to form a longitudinally-extending chamber when jaw members 410, 420 are moved to the approximated position. Channels 415, 425 may define half-circular front cross-sectional configurations such that, upon approximation of jaw members 410, 420, channels 415, 425 cooperate to define a cylindrical chamber extending longitudinally between jaw members 410, 420. Channels 415, 425 may extend completely along jaw members 410, 420, respectively, such that, as will be described below, a cutting tube 450 may be deployed from shaft 12

(FIG. 1) and into end effector assembly 400, through the cylindrical chamber defined by channels 415, 425, and may extend distally beyond a distal end 410b, 420b of jaw members 410, 420, respectively (see FIG. 10).

With reference now to FIGS. 9A-10, cutting tube 450 includes an elongated cylindrical body and defines a lumen 456 extending therethrough. Cylindrical cutting tube 450 is configured for translation through the cylindrical chamber extending through end effector assembly 400 when jaw members 410, 420 are in the approximated position. Distal end 454 of cutting tube 450 may include an angled distal tip 458 that may define a cutting edge 458. Cutting tube 450 may also include a rigid portion and a semi-rigid, or flexible portion. The rigid portion of cutting tube 450 may be disposed toward distal end 454 of cutting tube 450 to facilitate translation of culling tube 450 through jaw members 410, 420 to cut tissue disposed therebetween. The flexible, or semi-rigid portion of cutting tube 450 may permit articulation of cutting tube 450 when cutting tube 450 is extended beyond distal ends 410b, 420b of jaw members 410, 420, respectively. In one particular embodiment, cutting tube 450 may be configured as a hypotube.

Cutting tube 450 is initially disposed within shaft 12 (FIG. 1) in a retracted position. Cutting tube 450 is selectively translatable through end effector assembly 400, and may extend beyond distal ends 410b, 420b of jaw members 410, 420, respectively when translated to a fully extended position. A proximal end 452 of cutting tube 450 may be adapted to connect to a fluid source for delivering fluid through lumen 456 of cutting tube 450 to a surgical site, or area. Specifically, fluid, e.g., medicament, may be supplied through lumen 456 of cutting tube 450 to an area just beyond distal ends 410b, 420b of respective jaw members 410, 420 when cutting tube 450 is in the fully extended position. Alternatively, fluid may be supplied to tissue grasped between jaw members 410, 420 as cutting tube 450 cuts through tissue, for example, to reduce bleeding and/or to inhibit adhesion of tissue to end effector assembly 400. In addition to supplying fluid to a surgical area, cutting tube 450 may also be configured to operate in a suction mode for removing fluid from the surgical area.

In operation, as in the previous embodiment, tissue may be grasped between sealing surfaces 412, 422 of respective jaw members 410, 420 and electrosurgical energy may be supplied thereto for sealing tissue.

Additionally, as mentioned above, cutting tube 450 may be advanced through end effector assembly 400 from proximal ends 410a, 420a to distal ends 410b, 420b of jaw members 410, 420, respectively, for cutting tissue grasped therebetween and for supplying and/or removing fluid from the surgical site. More particularly, in regards to tissue cutting, or dissection, trigger 70 (FIG. 1) may be depressed to actuate deployment of cutting tube 450 from shaft 12 (FIG. 1) and between jaw members 410, 420. As cutting tube 450 is advanced through channels 415, 425 of jaw members 410, 420, respectively, angled distal cutting edge 458 cuts through tissue grasped between jaw members 410, 420. Alternatively, cutting tube 450 may be advanced to the fully extended position (where tissue is not disposed between jaw members 410, 420) such that angled distal cutting edge 458 extends distally from distal ends 410b, 420b of jaw members 410, 420, respectively. In such a position, end effector assembly 400 may be translated distally with respect to tissue to dissect tissue positioned distal of jaw members 410, 420 to reach a surgical site, or area.

As mentioned above, cutting tube 450 may be used to supply (or remove) fluid, e.g., gas and/or liquid, to tissue disposed between or positioned distal of jaw members 410, 420 of end effector assembly 400. Thus, end effector assembly 400 provides a single instrument, e.g., forceps 10, capable of sealing tissue, cutting tissue (tissue grasped between jaw members 410, 420 and tissue positioned distal of jaw members 410, 420), supplying fluids to a surgical site, and/or removing fluids from a surgical site.

Figure 11A:
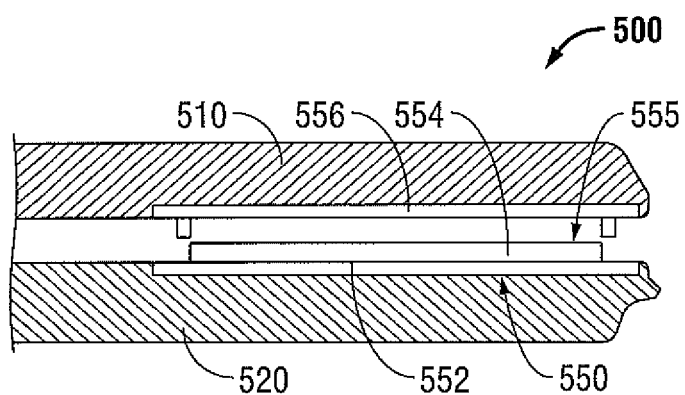
FIG. 11A is a side, cross-sectional view of an end effector assembly configure for use with the forceps of FIG. 1 according to still yet another embodiment of the present disclosure.
Figure 11B:
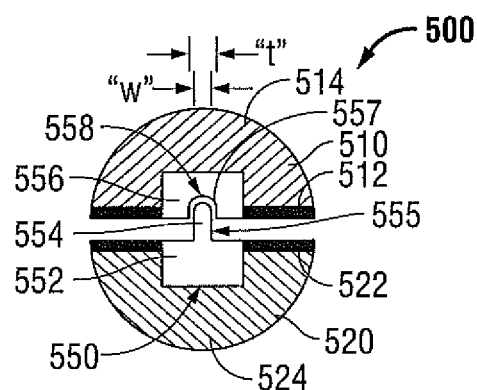
FIG. 11B is a front, cross-sectional view of the end effector assembly of FIG. 11A.

With reference now to FIGS. 11A-11B, yet another embodiment of an end effector assembly for use with forceps 10 (FIG. 1) is shown generally identified by reference numeral 500. End effector assembly 500 includes first and second jaw members 510, 520. Each jaw member 510, 520 includes a respective opposed sealing surface 512, 522 and an outer jaw housing 514, 524, respectively. Jaw members 510, 520 are moveable with respect to one another from a spaced-apart position to an approximated position for grasping tissue between sealing surfaces 512, 522 of jaw members 510, 520, respectively.

One jaw member, e.g., jaw member 520, includes a cutting member 550 disposed within a cavity defined therein and extending longitudinally therealong, while the other jaw member, e.g., jaw member 510, includes a sharpening block 556 disposed within a cavity defined therein and extending longitudinally therealong. As shown in FIGS. 11A-11B, jaw member 510 includes sharpening block 556 and jaw member 520 includes cutting member 550, although this configuration may be reversed.

Cutting member 550 includes a base 552 engaged within jaw member 520 and a blade 554 engaged to base 552 and extending from jaw member 520 toward jaw member 510. Blade 554 extends longitudinally along jaw member 520 and may be centered on jaw member 520. Blade 554 defines a width, or thickness "t," as shown in FIG. 11B.

Sharpening block 556 is disposed within jaw member 510 and is positioned opposite cutting member 550. A sharpening channel 558 is defined within block 556 and extends longitudinally along jaw member 510. Channel 558 defines a width "w" that is equal to or slightly less than the thickness "t" of blade 554 of cutting member 550. Alternatively, this configuration may be reversed, with the thickness of blade 554 being equal to or slightly less than the width of channel 558. Further, channel 558 may taper inwardly, defining a decreasing width from the open end to the closed end (the bottom of the channel) thereof.

Channel 558 of sharpening block 556 is configured such that, upon approximation of jaw members 510, 520, blade 554 of cutting member 550 is urged at least partially into channel 558 of sharpening block 556. As such, due to the relative dimensions of blade 554 and channel 558, blade 554 contacts the inner surface 557 of sharpening block 556 that defines channel 558 as jaw members 510, 520 are moved to the approximated position. In fact, as blade 554 is urged into channel 558, the outer peripheral surface 555 of blade 554 is sharpened upon contact with inner surface 557 of channel 558. In other words, the inner surface 557 of channel 558 defines a sheering or sharpening surface for sharpening the outer peripheral surface 555 of blade 554 as blade 554 is urged through channel 558. Additionally, the inner surface 557 of sharpening block 556 that defines channel 558 may include sharpening, or shearing features which facilitate the sharpening (or may be formed from a material that facilitates sharpening) of blade 554 upon the urging of blade 554 of cutting member 550 into channel 558 of sharpening block 556. Thus, as can be appreciated, blade 554 is sharpened each time jaw members 510, 520 are moved between the approximated and spaced-apart positions.

In operation, as in the previous embodiments, end effector assembly 500 is initially positioned such that tissue to be sealed and/or cut is disposed between jaw members 510 and 520. Next, jaw members 510, 520 may be moved from the spaced-apart position to the approximated position to grasp tissue between sealing surfaces 512, 522 of respective jaw members 510, 520. With jaw members 510, 520 in the approximated position, electrosurgical energy may be supplied to sealing surfaces 512, 522 of jaw members 510, 520, respectively, for sealing tissue. Simultaneously, or nearly simultaneously, as jaw members 510, 520 are moved to the approximated position, the sharpened blade 554 of cutting member 550 of jaw members 520 is translated through tissue to divide tissue disposed between jaw members 510, 520. Upon movement of jaw member 510, 520 to the fully approximated position, blade 554 is urged through tissue and into channel 558 of sharpening block 556 of jaw member 510 wherein blade 554 is sharpened.

Thus, end effector assembly 500 may be used to simultaneously or near-simultaneously, grasp, seal and divide tissue. Due to the self-sharpening, or shearing configuration of cutting member 550 and sharpening block 556, blade 554 is repeatedly sharpened with each successive cut. Accordingly, end effector assembly 500 may be used to efficiently and effectively grasp, seal and divide multiple vessels (or other tissue) in succession, without a decrease in effectiveness, e.g., blade dulling, as a result of repeated use.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A forceps, comprising:
    an end effector assembly including:
        first and second jaw members disposed in opposed relation relative to one another, at least one of the jaw members moveable with respect to the other between an open position and a closed position for grasping tissue therebetween;
        a knife channel defined within each of the jaw members and extending longitudinally therealong, each knife channel including a body portion and a base portion configured such that the knife channel defines a "T"-shaped configuration, wherein the body portion has a first width that is less than a second width of the base portion; and
    a knife assembly, the knife assembly including a knife having a bifurcated distal end and configured for translation through the body portions of the knife channels, the bifurcated distal end of the knife including first and second cutting members, each cutting member defining a cutting surface and having a tab extending transversely from a free end thereof, each tab complementarily-dimensioned to be retained within the base portion of one of the knife channels and configured for translation therethrough,
    wherein the knife is translatable into the knife channels of the jaw members when the jaw members are in the open or closed positions, the first and second cutting members of the knife in an approximated position with respect to one another when translated through the knife channels of the jaw members when the jaw members are in the closed position, the first and second cutting members flexed apart from one another in a spaced relation when translated through the knife channels of the jaw members when the jaw members are in the open position.

2. The forceps according to claim 1, wherein the first and second cutting members are resiliently moveable between the spaced-apart and approximated positions.

3. The forceps according to claim 1, wherein the first and second cutting members are biased toward the approximated position.

4. The forceps according to claim 1, wherein, when the first and second cutting members are disposed at a distal end of the knife channels, moving the jaw members between the open and closed positions produces a scissor-cutting effect on tissue disposed between the jaw members.

5. The forceps according to claim 1, wherein, when the first and second cutting members are translated through the knife channels with the jaw members in the closed position, the cutting members produce a dissection-cutting effect on tissue disposed between the jaw members.

6. The forceps according to claim 1, wherein at least one of the jaw members includes an electrically conductive tissue sealing surface disposed on an opposed surface thereof, the at least one sealing surface adapted to connect to a source of electrosurgical energy for sealing tissue disposed between the jaw members.

* * * * *